(12) United States Patent
Cuevas et al.

(10) Patent No.: US 10,172,867 B2
(45) Date of Patent: Jan. 8, 2019

(54) AFOBAZOLE NANOPARTICLES FORMULATION FOR ENHANCED THERAPEUTICS

(71) Applicants: Javier Cuevas, Lutz, FL (US); Christopher Katnik, Wesley Chapel, FL (US); Vijaykumar B. Sutariya, Tampa, FL (US)

(72) Inventors: Javier Cuevas, Lutz, FL (US); Christopher Katnik, Wesley Chapel, FL (US); Vijaykumar B. Sutariya, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/474,463

(22) Filed: Mar. 30, 2017

(65) Prior Publication Data
US 2017/0202848 A1 Jul. 20, 2017

Related U.S. Application Data (63) Continuation of application No. PCT/US2015/053537, filed on Oct. 1, 2015.

(60) Provisional application No. 62/058,405, filed on Oct. 1, 2014, provisional application No. 62/067,718, filed on Oct. 23, 2014.

(51) Int. Cl.
*A61K 31/5377* (2006.01)
*A61K 9/51* (2006.01)

(52) U.S. Cl.
CPC ........ *A61K 31/5377* (2013.01); *A61K 9/5146* (2013.01); *A61K 9/5153* (2013.01); *A61K 9/5169* (2013.01); *A61K 9/5192* (2013.01)

(58) Field of Classification Search
CPC . A61K 31/5377; A61K 9/5153; A61K 9/5192
See application file for complete search history.

(56) References Cited

U.S. PATENT DOCUMENTS

| | | |
|---|---|---|
| 6,645,528 B1 | 11/2003 | Straub et al. |
| 2013/0243832 A1 | 9/2013 | Turos et al. |
| 2014/0271903 A1 | 9/2014 | Sutariya et al. |
| 2015/0342883 A1* | 12/2015 | Cheng ................. A61K 31/704 424/1.37 |

FOREIGN PATENT DOCUMENTS

RU 2485954 C1 6/2013

OTHER PUBLICATIONS

Grover, A. et al. "Blood-Brain Barrier Permeation of Glutathione-Coated Nanoparticle" SOJ Pharm PharmSci 2014, 1(1), pp. 1-4. (Year: 2014).*
Anxiety Disorders (http://www.humanilinesses.com/original/A-As/Anxiety-Disorders.html) available Sep. 15, 2013. pp. 1-4. Year: (2013).*
Grover, A. et al. "Nanoparticle-Based Brain Targeted Delivery Systems" J Biomol Res Ther 2013, 2:2. (Year: 2013).*
Anxiety Disorders (http://www.humanillnesses.com/original/A-As/Anxiety-Disorders.html) available Sep. 15, 2013. pp. 1-4. (Year: 2013).*
Geldenhuys et al. "Brain-targeted delivery of paclitaxel using glutathione-coated nanoparticles for brain cancers"Journal of Drug Targeting, 2011; 19(9): 837-845 (Year: 2011).*
Hazai, I. et al. "Whole-body Autoradiography and Quantitative Organ-level Distribution Study of Deramciclane in Rats" J. Pharm. Pharmacol. 1999, 51: 165-174 (Year: 1999).*
Antipova, T.A. et al. "Effects of Selective Anxiolytic Afobazole on Active Caspase-3" Bulletin of Experimental Biology and Medicine, vol. 149, No. 2, Aug. 2010 (Year: 2010).*
Seredenin, S.B.; et al. "Antidepressant properties of afobazole in Porsolt and Nomura tests" Eksp Klin Farmakol. Jan.-Feb. 2009; 72(1): 19-21. (Year: 2009).*
Sahu, B.P. et al. "Nanosuspension for enhancement of oral bioavailability of felodipine" Appl Nanosci (2014) 4:189-197 (Year: 2014 ).*
Peletonen, L. et al. "The Effect of Cosolvents on the Formulation of Nanoparticles From Low-Molecular-Weight Poly(l)lactide" AAPS PharmSciTech 2002; 3 (4) article 32, pp. 1-7 (Year: 2002).*
Taglietti et al., Antibactrial Activity of Glutathione-Coated Silver Nanoparticles against Gram Positive and Gram Negative Bacteria. Langmuir. 2012. vol. 28: 8140-8148.
Soppimath et al., Biodegradable polymeric nanoparticles as drug delivery devices. J. Control. Release. 2001. vol. 70: 1-20.
Panyam and Labhasetwar. Biodegradable nanoparticles for drug and gene delivery to cells and tissue. Adv. Drug Deliv. Rev. 2003. vol. 55: 329-347.
Kumari et al., Biodegradable polymeric nanoparticles based drug delivery systems. Colloids Surf. B: Biointerfaces. 2010. vol. 75: 1-18.
Makadia et al., Poly Lactic-co-Glycolic Acid (PLGA) as Biodegradable Controlled Drug Delivery Carrier. Polymers. 2011. 3: 1377-1397.
Panagi et al, Effect of dose on the biodistribution and pharmacokinetics of PLGA and PLGA-mPEG nanoparticles. Int J Pharm. 2001. vol. 221: 143-152.
Bazile et al, Body distribution of fully biodegradable [14C]-poly(lactic acid) nanoparticles coated with albumin after parenteral administration to rats. Biomaterials. 1992. vol. 13 (No. 15): 1093-1102.

(Continued)

*Primary Examiner* — Andrew S Rosenthal
(74) *Attorney, Agent, or Firm* — Michele L. Lawson; Smith & Hopen, P.A.

(57) ABSTRACT

A novel nanoparticle drug composition and method of use thereof is presented herein. The nanoparticle drug composition is comprised of at least one nanoparticle carrier, formed from the conjugation of PLGA and PEG, which encapsulates a drug such as afobazole and its derivatives, in a pharmaceutically acceptable carrier. The nanoparticle drug composition may be used to treat various diseases of the central nervous system involving excessive neuronal activity and inflammation such as stroke, Alzheimer's disease and anxiety.

9 Claims, 4 Drawing Sheets

(56) References Cited

OTHER PUBLICATIONS

Grover et al., Blood-Brain Barrier Permeation of Glutathione-Coated Nanoparticle. SOJ Pharm PharmSci, 2014. vol. 1 (No. 1): 1-4.
Cuevas et al, Afobazole Modulates Neuronal Response to Ischemia and Acidosis via Activation of sigma-1 Receptors. JPET. 2011. vol. 339 (No. 1): 152-160.
Cuevas et al, Afobazole Modulates Microglial Function via Activation of Both sigma-1 and sigma-2 receptors. JPET. 2011. vol. 339 (No. 1): 161-172.
Katnik et al, Sigma-1 Receptor Activation Prevents Intracellular Calcium Dysregulation in Cortical Neurons during in Vitro Ischemia. JPET. 2006. vol. 319 (No. 3): 1355-1366.
Zenina et al., Neuroprotective Properties of Afobazol in Vitro. Bulleton of Experimental Biology and Medicine: Pharmacology and Toxicology. 2005. vol. 140 (No. 2): 194-196.
Antipova et al., Effects of Selective Anxiolytic Afobazole on Active Caspase-3. Bulletin of Experimental Biology and Medicine: Pharmacology and Toxicology. 2010. vol. 149 (No. 2): 201-203.
Mari et al, ASIC1a channels are activated by endogenous protons during ischemia and contribute to synergistic potentiation of intracellular Ca(2+) overload during ischemia and acidosis. Cell calcium. 2010. vol. 48: 70-82.
Coryell et al, Targeting ASIC1a reduces innate fear and alters neuronal activity in the fear circuit. Biological psychiatry. 200T vol. 62: 1140-1148.
Xiong et al., Neuroprotection in ischemia: blocking calcium-permeable acid-sensing ion channels. Cell. 2004. vol. 118: 687-698.
Seredenin et al., Internation of Afobazole with Sigma 1-Receptors. Bulletin of Experimental Biology and Medicine: Pharmacology and Toxicology. 2009. vol. 148 (No. 1): 42-44.
Translation of Russian Patent No. RU2485954 C1 (filed: Feb. 29, 2012) with a grant date of Jun. 27, 2013; Applicant: Federal state budget institution "Scientific Research Institute of Pharmacology named after W Zakusov" RAMS.
International Search Report and Written Opinion for PCT/US2015/053537 (filed Oct. 1, 2015) dated Dec. 28, 2015; Applicant: University of South Florida.
International Preliminary Report on Patentability for PCT/US2015/053537 (filed Oct. 1, 2015) with a priority date of Oct. 1, 2014; Applicant: University of South Florida et al.

\* cited by examiner

AFOBAZOLE NANOPARTICLES FORMULATION FOR ENHANCED THERAPEUTICS

CROSS REFERENCE TO RELATED APPLICATIONS

This application is a continuation of and claims priority to International Patent Application No. PCT/US2015/053537, entitled "Afobazole Nanoparticles Formulation For Enhanced Therapeutics", filed Oct. 1, 2015 by the same inventors, which claims priority to U.S. Provisional Patent Application No. 62/058,405, entitled "Afobazole Nanoparticles Formulation For Enhanced Therapeutics", filed Oct. 1, 2014, and U.S. Provisional Patent Application No. 62/067,718, entitled "Afobazole Nanoparticles Formulation For Enhanced Therapeutics", filed Oct. 23, 2014, the entire contents of each of which is herein incorporated into this disclosure.

FIELD OF INVENTION

This invention relates to drug formulations. Specifically, the invention describes a novel nanoparticle formulation of afobazole.

BACKGROUND OF THE INVENTION

The use of biodegradable polymeric nanoparticles is one way to reduce drug toxicity and degradation, while enhancing the residence time and drug concentration at the desired site of action. Biodegradability is an important attribute of a nanoparticle carrier for several reasons, including the ability to control the release of the bound molecule in a sustained, programmable way, and to provide the means for the final removal of the carrier from the body in an innocuous form. (K. S. Soppimath, T. M. Aminabhavi, A. R. Kulkarni, W. E. Rudzinski, Biodegradable polymeric nanoparticles as drug delivery devices, J. Control. Release 70 (1-2) (2001) 1-20; J. Panyam, V. Labhasetwar, Biodegradable nanoparticles for drug and gene delivery to cells and tissue, Adv. Drug Deliv. Rev. 55 (3) (2003) 329-347; A. Kumari, S. K. Yadav, S. C. Yadav, Biodegradable polymeric nanoparticles based drug delivery systems, Colloids Surf. B: Biointerfaces 75 (1) (2010) 1-18).

Biodegradable materials may be natural or synthetic and are degraded hi vivo, either enzymatically or non-enzymatically or both, to produce biocompatible, toxicologically safe by-products which are further eliminated by the normal metabolic pathways. Biomaterials used in drug delivery can be broadly classified as (1) synthetic biodegradable polymers, which includes relatively hydrophobic materials such as the a-hydroxy acids (a family that includes poly lactic-co-glycolic acid, PLGA), polyanhydrides, and others, and (2) naturally occurring polymers, such as complex sugars (hyaluronan, chitosan) and inorganics (hydroxyapatite). (Makadia H. K., et al., Poly Lactic-co-Glycolic Acid (PLGA) as Biodegradable Controlled Drug Delivery Carrier, Polymers (Basel), 2011, 3(3): 1377-1397).

Polyester PLGA is a copolymer of poly lactic acid (PLA) and poly glycolic acid (PGA). Poly lactic acid contains an asymmetric a-carbon which is typically described as the D or L form in classical stereochemical terms and sometimes as R and S form, respectively. The enantiomeric forms of the polymer PLA are poly D-lactic acid (PDLA) and poly L-lactic acid (PLLA). PLGA is generally an acronym for poly D,L-lactic-co-glycolic acid where D- and L-lactic acid forms are in equal ratio. (Makadia et al, 2011)

PLGA can be processed into almost any shape and size, and can encapsulate molecules of virtually any size. It is soluble in wide range of common solvents including chlorinated solvents, tetrahydofuran, acetone or ethyl acetate. In water, PLGA biodegrades by hydrolysis of its ester linkages. Due to the hydrolysis of PLGA, parameters that are typically considered invariant in a solid formulation can change with time, such as the glass transition temperature (Tg), moisture content and molecular weight. The change in PLGA properties during polymer biodegradation influences the release and degradation rates of incorporated drug molecules. PLGA physical properties themselves depend upon multiple factors, including the initial molecular weight, the ratio of lactide to glycolide, the size of the device, exposure to water (surface shape) and storage temperature. Mechanical strength of the PLGA is affected by physical properties such as molecular weight and polydispersity index. These properties also affect the ability to be formulated as a drug delivery device and may control the device degradation rate and hydrolysis. The type of drug may also play a role in setting the release rate. Mechanical strength, swelling behavior, capacity to undergo hydrolysis and subsequently biodegradation rate of the polymer are directly influenced by the degree of crystallinity of the PLGA, which is further dependent on the type and molar ratio of the individual monomer components in the copolymer chain. Crystalline PGA, when co-polymerized with PLA, reduces the degree of crystallinity of PLGA and as a result increase the rate of hydration and hydrolysis. As a rule, higher content of PGA leads to quicker rates of degradation with an exception of 50:50 ratio of PLA/PGA, which exhibits the fastest degradation, with higher PGA content leading to increased degradation interval below 50%. Degree of crystallinity and melting point of the polymers are directly related to the molecular weight of the polymer. The Tg (glass transition temperature) of the PLGA. copolymers are reported to be above the physiological temperature of 37° C. and hence are glassy in nature, thus exhibiting fairly rigid chain structure. The Tg of PLGAs decrease with a decrease of lactide content in the copolymer composition and with a decrease in molecular weight. (Makadia et al. 2011)

Various types of block copolymers of polyesters with poly ethylene glycol (PEG) have been developed in response to the need for better delivery formulations to incorporate a variety of drugs and methods of administration. PL-GA/PEG block copolymers can be processed as a diblock (PLGA-PEG) or tri-block (PLGA-PEG-PLGA) molecules. In diblock types, PEG chains orient themselves towards the external aqueous phase in micelles, thus surrounding the encapsulated species. This layer of PEG acts as a barrier and reduces the interactions with foreign molecules by steric and hydrated repulsion, giving enhanced shelf stability. (Makadia et al, 2011)

PLGA copolymer undergoes degradation by hydrolysis or biodegradation through cleavage of its backbone ester linkages into oligomers and, finally monomers. The degradation process for these polymers is mainly through uniform bulk degradation of the matrix where the water penetration into the matrix is higher than the rate of polymer degradation. Furthermore, the increase of carboxylic end groups as a result of biodegradation autocatalyses the process. The degradation of PLGA copolymer is the collective process of bulk diffusion, surface diffusion, bulk erosion and surface erosion. Since there are many variables that influence the degradation process, the release rate pattern is often unpredictable. The biodegradation rate of the PLGA copolymers are dependent on the molar ratio of the lactic and glycolic acids in the polymer chain, molecular weight of the polymer, the degree of crystallinity, and the Tg of the polymer. The release of drug from the homogeneously degrading matrix is more complicated. In general, the initial burst of drug release is related to drug type, drug concentration and polymer hydrophobicity. Drug on the surface, in contact with the medium, is released as a function of solubility as well as penetration of water into polymer matrix. Random scission of PLGA decreases molecular weight of polymer significantly, but no appreciable weight loss and no soluble monomer product are formed in this phase. In the second phase, drug is released progressively through the thicker drug depleted layer. The water inside the matrix hydrolyzes the polymer into soluble oligomeric and monomeric products. This creates a passage for drug to be released by diffusion and erosion until complete polymer solubilization. Drug type also plays an important role here in attracting the aqueous phase into the matrix. (Makadia et al. 2011)

Several factors can affect degradation of PLGA nanoparticles including: polymer composition; crystallinity; weight average molecular weight of the polymer; type of drug; ratio of surface area to volume of the polymer; pH; and drug loading, In general, the PLGA degradation and the drug release rate can be accelerated by greater hydrophilicity, increase in chemical interactions among the hydrolytic groups, less crystallinity and larger volume to surface ratio of the device, (Makadi a et al. 2011)

Previous studies suggest that both blood clearance and uptake by the mononuclear phagocyte system (MPS) may depend on dose and composition of PLGA carrier systems. (Panagi Z., et al., Effect of dose on the biodistribution and pharmacokinetics of PLGA and PLGA-mPEG nanoparticles. *Int J Pharm.*, 2001 Jun. 19; 221(1-2): 143-52). The degradation of the PLGA carriers is quick on the initial stage (around 30%) and slows eventually to be cleared by respiration in the lung. (Bazile D V, et al., Body distribution of fully biodegradable [14C]-poly(lactic acid) nanoparticles coated with albumin after parenteral administration to rats. *Biomaterials*, 1992; 13(15): 1093-102). Surface modification via incorporation of surface modifying agents can significantly increase blood circulation half-life. (Makadia et al. 2011)

Glutathione (GSH) is a tripeptide antioxidant that protects tissues from reactive oxidative species (ROS) as well as other types of oxidative damage. GSH interacts with transmembrane proteins located in the brain that are involved in the active transport of certain substances across the blood brain barrier (BBB). The BBB is a physical interface in the central nervous system (CNS) between the blood and nervous tissue which greatly limits the availability of drugs to the brain. Coating drug-encapsulating nanoparticles with glutathione facilitates the nanoparticles crossing the BBB which allows for targeted therapies of brain-related disorders. (Grover A., et al., Blood-Brain Barrier Permeation of Glautathione-Coated Nanoparticle, *SOJ Pharm PharmSci*, 2014, 1(1):4)

Afobazole (5-ethoxy-2[2-(morpholine)-ethylthio]benzimidazole), a drug currently used in Russia to treat anxiety and panic disorders, was recently shown to be both a σ-1 and σ-2 receptor agonist, and provides neuroprotection in an in vitro ischemia model (Cuevas et al., 2011a; Cuevas et al., 2011b). Unlike ANAVEX2-73, afobazole does not interact with muscarinic receptors (Seredenin et al., 2009).

Activation of σ-1 receptors by afobazole results in a decrease in ischemia-induced $Ca^{2+}$ overload, which is due in part to inhibition of NMDA channel activation (Katnik et al., 2006; Cuevas et al., 2011a). Previous studies have suggested other mechanisms for the neuroprotective properties of afobazole, including decreased caspase-3 activation and reduced oxidative stress (Zenina et al., 2005; Antipova et al., 2010).

Afobazole currently has a short half-life in vivo and has limited brain penetration. This drug is currently used in once a day dosing for the treatment of anxiety in Europe and is being studied for the treatment of other diseases such as stroke, multiple sclerosis and Alzheimer's disease.

Given the obstacles of treatment with afobazole as described above, what is needed is a drug formulation which can readily cross the blood brain barrier (BBB) and enhance the residence time and drug concentration at the targeted site.

SUMMARY OF INVENTION

The current invention involves the use of nanoparticle technology to improve pharmacokinetics and pharmacodynamics of afobazole.

In an embodiment, a nanoparticle drug composition is presented comprising: at least one nanoparticle carrier comprising a polylactic-co-glycolic acid) biocornpatible polymer conjugated to an amphiphilic polyol; a pharmaceutically active agent encapsulated within the at least one nanoparticle carrier wherein the pharmaceutically active agent is afobazole or its derivatives; and a pharmaceutically acceptable carrier.

The composition can further comprise a hydrophilic antioxidant coated on the nanoparticle carrier wherein the hydrophilic antioxidant is glutathione. The amphiphilic polyol can be polyethylene glycol. The nanoparticle may have a mean particle size of between about 100 nm and about 250 nm.

In a further embodiment, a method of treating a central nervous system disorder in a patient in need thereof is presented comprising: administering a therapeutically effective amount of a nanoparticle drug composition wherein the nanoparticle drug composition comprises: at least one nanoparticle carrier comprising a poly(lactic-co-glycolic acid) biocompatible polymer conjugated to an amphiphilic polyol; a pharmaceutically active agent encapsulated within the at least one nanoparticle carrier wherein the pharmaceutically active agent is afobazole or its derivatives; and a pharmaceutically acceptable carrier.

The composition can further comprise a hydrophilic antioxidant coated on the nanoparticle carrier wherein the hydrophilic antioxidant is glutathione. The amphiphilic polyol can be polyethylene glycol. The nanoparticle may have a mean particle size of between about 100 nm and about 250 nm. The central nervous system disorder can be characterized by excessive neuronal activity or inflammation such as in ischemic, Alzheimer's disease, multiple sclerosis and anxiety.

In another embodiment, a method of generating a nanoparticle suspension is presented comprising: nanoprecipitation of a polymer, further comprising: dissolving or diluting poly(lactic-co-glycolic acid) conjugated with polyethylene glycol (PLGA-PEG) in acetone to form a solution; dissolving a predetermined quantity of a drug such as afobazole in ethanol to form a drug solution; adding the drug solution to the PLGA-PEG solution to form an organic phase solution; adding the organic phase solution to deionized water to form a mixture; stirring the mixture; evaporating the acetone from the mixture wherein upon evaporation of the acetone a suspension of nanoparticles is generated; and coating the suspension of nanoparticles with a hydrophilic antioxidant such as glutathione. In some cases the acetone is evaporated overnight at room temperature.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise.

"Patient" is used to describe an animal, preferably a human, to whom treatment is administered, including prophylactic treatment with the compositions of the present invention.

The "therapeutically effective amount" for purposes herein is thus determined by such considerations as are known in the art. A therapeutically effective amount of the compositions or any combination thereof is that amount necessary to provide a therapeutically effective result in vivo or in vitro, including, but not limited to, total prevention of (e.g., protection against) and to improved survival rate or more rapid recovery, or improvement or elimination of symptoms associated with neurodegenerative disorders, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

"Administration" or "administering" is used to describe the process by which the compounds of the present invention, or any combination thereof, are delivered to a patient. The composition may be administered in various ways including parenteral (referring to intravenous and intraarterial and other appropriate parenteral routes), intratheceal, intraventricular, intracisternal, intranigral, oral, transdermally, subcutaneously, and other routes that allow the composition to contact neurons. The compositions of the invention may be administered independently or in combination with other compounds. Administration will often depend on the disease and level of progression in the afflicted brain.

The terms "pharmaceutical compositions", "drugs", "agents" and "compounds" are used interchangeably herein to refer to a molecule, a group of molecules, a complex or substance containing an active agent that is administered to a subject for diagnostic, therapeutic, preventative, medical, or veterinary purposes. Included are externally and internally administered topical, localized and systemic human and animal pharmaceuticals, treatments, remedies, nutraceuticals, biologicals, and diagnostics, including preparations useful in clinical and veterinary screening, prevention, prophylaxis, healing, wellness, detection, imaging, diagnosis, therapy, surgery, monitoring, and the like.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, $19^{th}$ ed.) describes formulations which can be used in connection with the subject invention.

For ease of administration, the subject compounds may be formulated into various pharmaceutical forms. As appropriate compositions there may be cited all compositions usually employed for systemically or topically administering drugs. To prepare the pharmaceutical compositions of this invention, the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, vaginally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, as a spot-on or as an ointment.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. A preferred dose can be adjusted downward to establish a minimum dosage in vivo and can be adjusted upwards to establish a maximum dosage in vivo for the present invention as is known by those of skill in the art.

The compounds used in the present invention may be administered individually, or in combination with or concurrently/concomitantly with one or more other compounds used in other embodiments of the present invention.

The term "composition" as used herein encompasses a product comprising the specified ingredients in the specified amounts, as well as any product which results, directly or indirectly, from combination of the specified ingredients in the specified amounts.

The term "nanoparticle" as used herein refers to a particle or structure which is biocompatible with and sufficiently resistant to chemical and/or physical destruction by the environment of such use so that a sufficient number of the nanoparticles remain substantially intact after delivery to the site of application or treatment and whose size is in the nanometer range. For the purposes of the present invention, a nanoparticle typically ranges between about 1 nm to about 1000 nm, preferably between about 50 nm and about 500 nm, more preferably between about 50 nm and about 350 nm, more preferably between about 100 nm and about 250 nm. The terms "nanoparticle" and "nanostructure" are used interchangeably herein.

The term "nanoprecipitation" as used herein refers to the process of forming nanoparticles through solvent displacement. In nanoprecipitation, pre-formed polymers are converted into nanoparticles by dissolving the polymer in a water-miscible organic solvent and adding this solution to water. Generally, here, poly(lactic-co-glycolic acid) (PLGA) conjugated with polyethylene glycol (PEG) (PLGA-PEG) was dissolved in acetone to form a PLGA solution. 3 mg of Afobazole was dissolved in 280 of ethanol and subsequently added in 20 □l increments to the PLGA solution. This resulting solution (organic phase) was added dropwise to 8 mL of deionized H2O spinning at 600 rpm overnight to allow the full evaporation of the organic phase and the formation of the NP suspension. The NPs were separated by centrifugation at 5,000 rpm for 30 minutes and resuspended in 10 ml of fresh deionized H2O.

The term "drug" as used herein refers to a chemical entity of varying molecular size, small and large, naturally occurring or synthetic, that exhibits a therapeutic effect in animals and humans. A drug may include, but is not limited to, a therapeutic protein, peptide, antigen, or other biomolecule. A drug useful with the nanoparticle composition described herein is afobazole and its derivatives.

The term "degradation" as used herein refers to the surface and bulk erosion of the polymer.

The term "pharmaceutically active agent" as used herein refers to a molecule, a group of molecules, a complex or substance that is administered to a subject for diagnostic, therapeutic, preventative, medical, or veterinary purposes and includes drugs and vaccines. Included are externally and internally administered topical, localized and systemic human and animal pharmaceuticals, treatments, remedies, nutraceuticals, cosmeceuticals, biologicals, and diagnostics, including preparations useful in clinical and veterinary screening, prevention, prophylaxis, healing, wellness, detection, imaging, diagnosis, therapy, surgery, monitoring, cosmetics, forensics, and the like.

The term "polymer" as used herein refers to a relatively high molecular weight organic compound, natural or synthetic, whose structure can be represented by a repeated small unit, the monomer. Synthetic polymers are typically formed by addition or condensation polymerization of monomers. The polymers used or produced in the present invention are biodegradable. The polymer is suitable for use in the body of a subject, i.e. is biologically inert and physiologically acceptable, non-toxic, and is biodegradable in the environment of use, i.e. can be resorbed by the body. Examples of synthetic polymers include, but are not limited to, poly-lactic acid (PLA); polycaprolactone (PCL); polystyrene (PS); polyacrylamide; polyacrylate; poly (alkyl cyanoacrylates); poly (isobutyl cyanoacrylates); poly (butylcyanoacrylates); poly methyl (methcyanoacrylates); and combinations thereof.

The term "copolymer" as used herein refers to a polymer formed from two or more different repeating units (monomer residues). A "block copolymer" is a polymer formed from multiple sequences or blocks of the same monomer alternating in series with different monomer blocks. Block copolymers are classified according to the number of blocks they contain and how the blocks are arranged.

The term "polyol" as used herein refers to an alcohol that contains multiple hydroxyl groups. Examples of polyols include, but are not limited to, polyethylene glycol, polypropylene glycol, glycerin, and combinations thereof.

The term "amphiphilic" as used herein refers to a compound having both hydrophilic and hydrophobic (lipophilic) groups.

The term "antioxidant" as used herein refers to a molecule that is capable of slowing or preventing the oxidation of other molecules. Hydrophilic antioxidants include glutathione, uric acid, ascorbic acid, thiols, proteoglycans, and hyaluronic acid. Examples of antioxidants that may be used to coat the nanoparticles of the instant invention include, but are not limited to, glutathione and thiamine.

The inventors have identified a new formulation of a drug using nanoparticle technology. This drug may be used to treat various diseases of the central nervous system involving excessive neuronal activity and inflammation. In vitro experiments show that the nanoparticle formulation of the drug enhances the effectiveness of this drug for protecting neurons from ischemic injury.

Poly(lactic-co-glycolic acid) (PLGA) conjugated with polyethylene glycol (PEG) (PLGA-PEG) (5050 DLG, mPEG 5000, 5wt % PEG) was purchased from Lakeshore Biomaterials (Birmingham, Ala.). Glutathione (GSH) (reduced) was purchased from Fisher Bioreagents. Phosphate buffered saline (PBS) solution was purchased from Cellgro (Corning Inc., NY). Thiazolyl blue tetrazolium bromide (MTT reagent), acetone and methanol were both purchased from Sigma-Aldrich. All other chemicals used in the study were of analytical grade and were used without any further purification unless specified.

Afobazole NPs were prepared using a nanoprecipitation method. Briefly, 120 mg PLGA-PEG were dissolved in 4 ml acetone. 3 mg of Afobazole was dissolved in 280 □l of ethanol and then added in 20 □l increments to the PLGA solution. This resulting solution (organic phase) was added dropwise to 8 mL of deionized H2O spinning at 600 rpm overnight to allow the full evaporation of the organic phase and the formation of the NP suspension. The NPs were separated by centrifugation at 5,000 rpm for 30 minutes and resuspended in 10 ml of fresh deionized H2O.

For the GSH-coated afobazole nanoparticles (GSH-Afo NP), the nanoparticles described above were subsequently coated with glutathione (GSH) by adding reduced GSH (10 mg) to 1 ml of NP solution to result in a 1% w/v final concentration. This novel coating method was used in order to enhance the blood-brain barrier (BBB) permeation of the nanoparticles via GSH-transporters present on the BBB.

Statistical Analysis:

Assessed using paired student's t-test with significance ($p<0.05$). All experiments were performed in three replicates for statistical significance and all the values are represented as mean of three separate measurements ±SD.

NPs Characterization:

The NP parameters were studied by measuring the particle size and polydispersity index (PDI). The effect of a 1% GSH coating on the NP was studied by comparing Afobazole nanoparticles (Afo NPs) to the glutathione-coated Afobazole nanoparticles (GSH-Afo NPs). The particle size and polydispersity index was measured using DynamicPro plate reader. Wyatt Technology, CA, USA. The NPs samples were diluted 1:100 in deionized water to fit instrument specifications.

TABLE 1

|  | Size | PDI |
|---|---|---|
| Afobazole NPs | 233.83 ± 6.137 | 0.045 ± 0.030 |
| GSH-Afobazole NPs | 142.63 ± 8.949 | 0.01 ± 0.003 |

Afo NPs have an average size of 233.83 nm and the GSH-Afo NPs have an average particle size of 142.63 nm.

The smaller size of the GSH-Afo NPs as compared to the Afo NPs may be attributed to (1) the GSH coating of the NPs which may induce a more compact shape due to the electrostatic interactions of the GSH, NPs coat, and encapsulated drug molecules; and (2) displacement of any Afo existing on the surface of the NPs by GSH The sizes of NPs in each formulation were normally distributed as suggested by PDI data.

Figure 1:
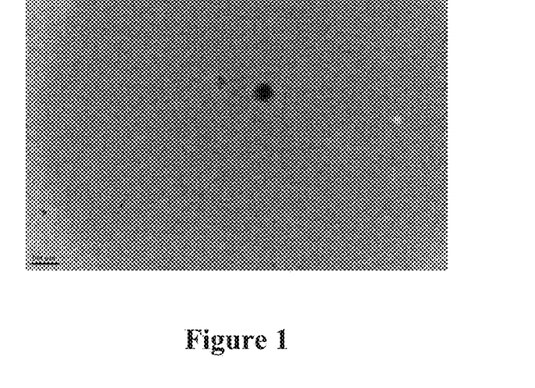
FIG. 1 is a transmission electron microscopy (TEM) image depicting the morphology of a nanoparticle (not loaded with drug). As shown in the image, the nanoparticle is spherical in shape and is smaller than 200 nm.

NPs Morphology:

Examination of nanoparticles morphology, size and shape, was conducted via transmission electron microscopy (TEM) using a JEOL 100S TEM (JEOL Ltd, Tokyo, Japan). Following particle sizing, sample was diluted 100 times and 10 μL of the NP solution was carefully placed onto a copper grid coated in a nitrocellulose membrane. The diluted nanoparticle preparation was placed on the nitrocellulose membrane to allow for optimal viewing of the nanoparticle size and morphology.

In Vitro Release:

The rate of afobazolle release from the nanoparticles was measured by an in vitro release assay. Dialysis membranes (MWCO 10,000 Da, Spectrum Laboratories, CA, USA) were soaked in DI water overnight. The nanoparticles were sonnicated briefly. 1 ml of the NP suspension was added to dialysis membrane tubing which was placed in 100 mL of phosphate buffered saline (PBS); solution was covered and spun at 100 rpm at 37° C. 1.5 mL aliquots were removed at predetermined intervals and replaced with fresh PBS solution. Aliquots were analyzed using UV spectroscopy at a wavelength of 298 nm (λmax) and compared to analyzed standard dilutions to determine the percentage of drug released over 14 days for both Afo NPs, and GSH-Afo NPs.

Figure 2:
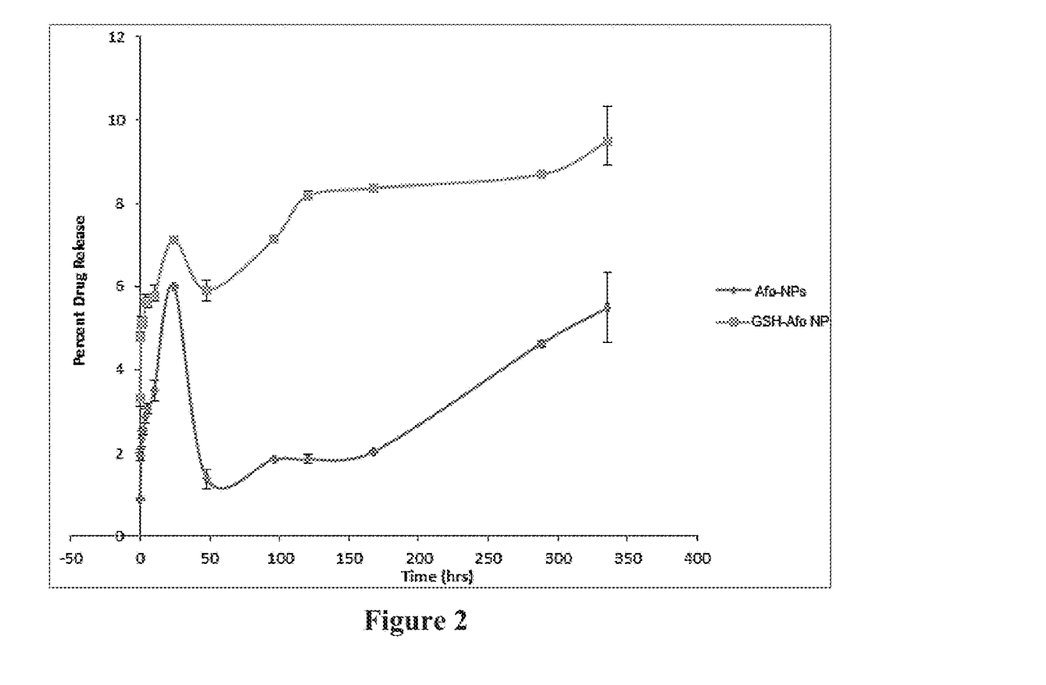
FIG. 2 is a graph depicting the rate of drug release by the nanoparticle formulations. 2 samples were studied, Afo NPs, and GSH-Afo NPs over 14 days. Both NPs formulations showed an initial burst release of the drug (due to any unencapsulated drug on the surface of NP) followed by a sustained release of the drug from the NPs polymer. Samples were read in triplicate (n=3) and reported as mean percent drug release ±SD.

Both NP formulations showed an initial burst release of the drug (due to any unencapsulated drug on the surface of NP) followed by a sustained release of the drug from the NPs polymer. Samples were read in triplicate (n=3) and reported as mean percent drug release ±SD. (FIG. 2)

Drug release from NPs polymers occurs mainly through diffusion and swelling-induced lysing of the NPs matrix. In addition, the long chains of the PEG-PLGA polymer induce the attraction of water molecules to the NPs matrix to enter the NPs and release drug through hydration. The rapid release of drug from the GSH-Afo NPs may be induced by greater attraction of water by the hydrophilic GSH-coated surface of the GSH-Afo NPs. This attraction leads to greater hydration and release of drug from the NPs matrix.

Figure 3:
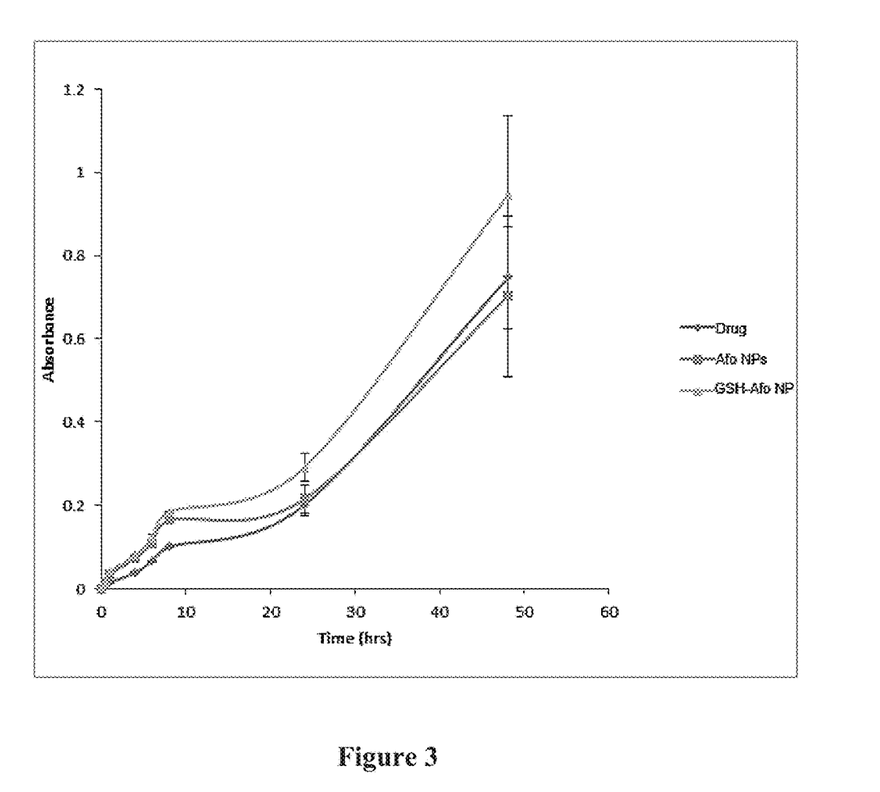
FIG. 3 is a graph depicting the blood-brain barrier permeability of afobazole nanoparticles and glutathione-coated afobazole nanoparticles. The samples were analyzed using UV spectroscopy at a wavelength of 298 nm (λmax).

Blood-Brain Barrier:

A Transwell™ model was established to investigate the trans-BBB permeability potential of equivalent concentrations of NP formulations (Afo-NPs and GSH-Afo NPs) as compared to aqueous drug solution over a 48 hour study period (FIG. 3). Transwell™ permeable supports with 0.4 μm porous membrane (Corning Inc., NY) were purchased and both sides were coated with 0.1% rat tail collagen I (BD Biosciences™). Inserts were seeded with RBE4 rat brain endothelial cells and C6 rat glioma cells. Drug solution, Afo-NPs, and GSH-Afo NPs were added to the apical side of the insert and 100 μL samples were collected and replaced with fresh medium from the lower chamber at predetermined time intervals. The samples were analyzed by UV spectroscopy at a wavelength of 298 nm (λmax) (FIG. 3).

Figure 4:
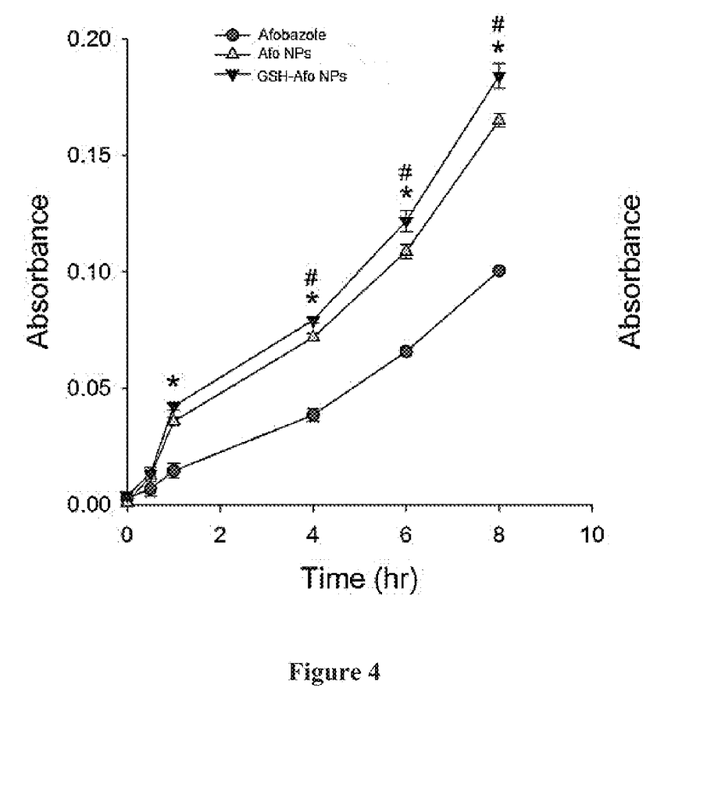
FIG. 4 is a graph depicting the trans-BBB permeability potential of equivalent concentrations of NP formulations as compared to aqueous drug solution over the first 8 hr period showed that both NP formulations have significantly greater permeability than the aqueous afobazole (*). Furthermore, the afobazole GSH NP formulation had greater permeability than the afobazole NP preparation (#) from 4 to 8 hrs (p<0.001 and n=4 for all).

The permeation profiles of the drug solution and both NP preparations were relatively similar for the first 24 hours of the study. Focusing on the trans-BBB permeability potential of equivalent concentrations of NP formulations as compared to aqueous drug solution over the first 8 hr period showed that both NP formulations have significantly greater permeability than the aqueous afobazole (*). Furthermore, the GSH-Afo NPs formulation had greater permeability than the Afo NPs (#) from 4 to 8 hrs (p<0.001 and n=4 for all). (FIG. 4) At the end of the 48 hour study period, the GSH-Afo NPs showed the greatest permeation through the BBB model. The greater rate of GSH-Afo NP permeation is likely due to the presence of GSH receptors on the BBB that allow for increased endocytosis by the endothelial cells to allow passage through the BBB.

The enhanced BBB permeability, and thus more favorable pharmacokinetics, of the nanoparticle formulations can improve in vivo efficacy of this drug for the treatment of CNS disorders such as anxiety, stroke and Alzheimer's disease.

In Vitro Ischemia

Experiments were conducted to determine if the NP formulation of afobazole affected. ischemia+acidosis induced elevation in neuronal calcium, which have been linked to ischemic death. Fluorometric $Ca^{2+}$ imaging using fura-2 was carried out in isolated cortical neurons from embryonic day 18 rats as previously reported (Mari Y, Katnik C and Cuevas J (2010) ASIC 1a channels are activated by endogenous protons during ischemia and contribute to synergistic potentiation of intracellular Ca(2+) overload during ischemia and acidosis. *Cell calcium* 48:70-82). Neurons were cultured for 10-18 days and bathed in a physiological saline solution (PSS) containing (in mM): 140 NaCl, 3 KCl, 1.4 $CaCl_2$, 1.0 $MgCl_2$, 7.7 glucose, and 10 HEPES (pH to 7.4 with NaOH). Ischemia+acidosis was evoked by applying PSS at pH 6.5 with no glucose and 4 mM sodium azide.

Figure 5:
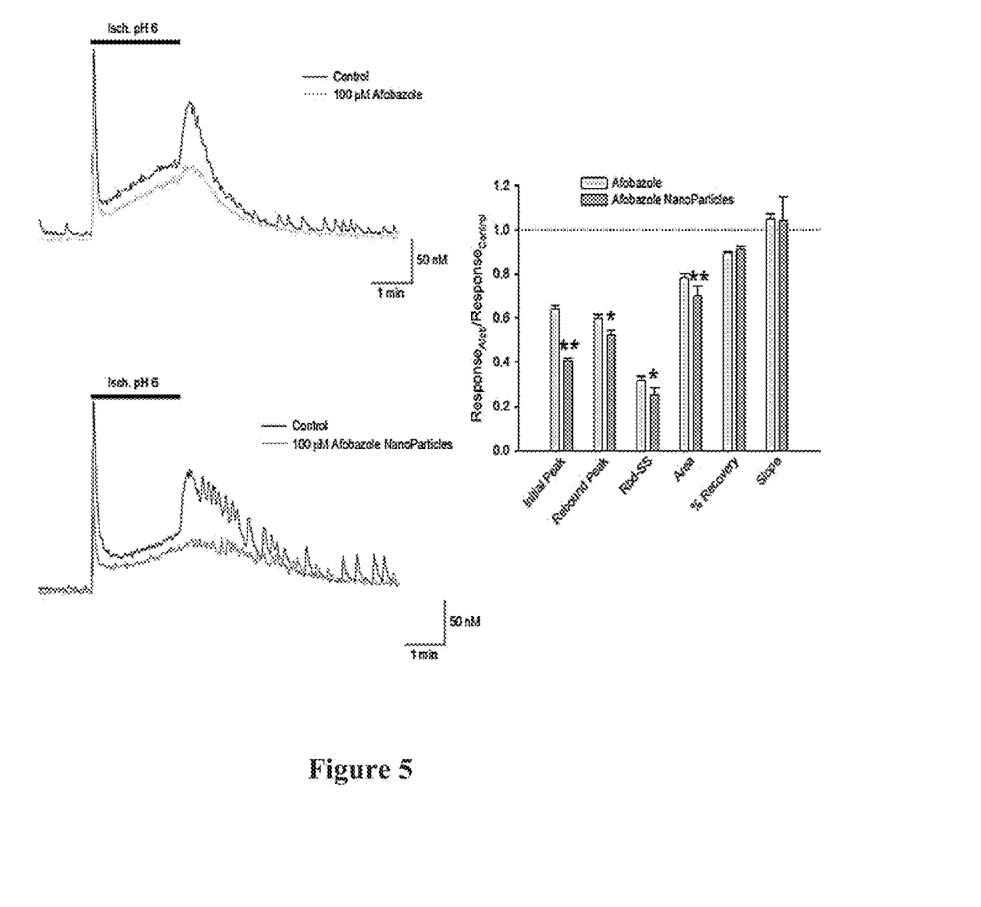
FIG. 5 is a series of images depicting that the NP formulation of afobazole was found to inhibit multiple phases of the calcium overload produced by ischemia+ acidosis. Relative to conventional afobazole, the NP formulation yielded superior results, with peak calcium, rebound calcium (reperfusion-associated) and net calcium (area) decreased to a greater extent by the NP formulation.

Application of ischemia evoked a rapid, transient rise in intracellular $Ca^{2+}([Ca^{2+}]_i)$, that was followed by a slow increase in $[Ca^{2+}]_i$. Upon addition of normal PSS (reperfusion) there was a transient elevation in $[Ca^{2+}]_i$. The Afo-NPs was found to inhibit multiple phases of the calcium overload produced by ischemia +acidosis. Relative to conventional afobazole, the Afo-NP formulation yielded superior results, with peak calcium, rebound. calcium (reperfusion-associated) and net calcium (area) decreased to a greater extent by the NP formulation. (FIG. 5) While the GSH-Afo NPs were not specifically tested in vitro, they are predicted to show benefit due to their ability to cross the BBB and target the brain. These two factors are not limiting in the in vitro model since the drug is being directly applied to the neurons.

It is important to note that the initial transient peak increase in $[Ca^{2+}]_i$ is due to the activation of ASIC 1a and resulting membrane depolarization (Mari Y, Katnik C and Cuevas J (2010) ASIC1a channels are activated by endogenous protons during ischemia and contribute to synergistic potentiation of intracellular Ca.(2+) overload during ischemic and acidosis. *Cell calcium* 48:70-82). inhibition of ASIC1a has been shown to decrease anxiety and provide neuroprotection following ischemic stroke ((Coryell M W, Ziemann A E, Westmoreland P J, Haenfler J M, Kurjakovic Z, Zha X M, Price M, Schnizler M K and Wemmie J A (2007) Targeting ASIC1a reduces innate fear and alters neuronal activity in the fear circuit. *Biological psychiatry* 62:1140-1148; Xiong Z G, Zhu X M, Chu X P, Minami M, Hey J, Wei W L, MacDonald J F, Wemmie J A, Price M P, Welsh M J and Simon R P (2004) Neuroprotection in ischemia: blocking calcium-permeable acid-sensing ion channels. *Cell* 118:687-698.) Thus, the increased efficacy of the NP formulation is predicted to improve outcomes in multiple disease states in which afobazole is beneficial.

In conclusion, the inventors have developed a new nanoparticle composition and its associated method of use using the drug afobazole and its derivatives encapsulated within a PLGA-PEG nanoparticle that may be coated with glutathione to increase permeability through the blood-brain barrier. It was found that encapsulation of the drug within nanoparticles greatly enhanced the half-life of the drug which is beneficial in targeted drug therapies for patients having diseases of the central nervous system.

It is also to be understood that the following claims are intended to cover all of the generic and specific features of the invention herein described, and all statements of the scope of the invention which, as a matter of language, might be said to fall there between. Now that the invention has been described.

What is claimed is:

1. A nanoparticle drug composition comprising:
   at least one nanoparticle carrier comprising a poly(lactic-co-glycolic acid) polymer conjugated to polyethylene glycol wherein the nanoparticle carrier is coated with glutathione; and
   a pharmaceutically active agent encapsulated within the at least one nanoparticle carrier wherein the pharmaceutically active agent is afobazole;
   wherein the nanoparticle drug composition is generated by the process consisting essentially of:
      dissolving or diluting the poly(lactic-co-glycolic acid) conjugated to the amphiphilic polyol in acetone to form a polymer solution;
      dissolving a predetermined quantity of the afobazole in ethanol to form a drug solution;
      adding the drug solution to the polymer solution to form an organic phase solution;
      adding the organic phase solution to deionized water to form a mixture;
      stirring the mixture;
      evaporating the acetone from the mixture wherein upon evaporation of the acetone a suspension of nanoparticles is generated; and
      coating the suspension of nanoparticles with the glutathione.

2. The composition of claim 1, wherein the nanoparticle carrier has a mean particle size of between about 100 nm and about 250 nm.

3. A method of treating a central nervous system disorder in a patient in need thereof comprising: administering a therapeutically effective amount of a nanoparticle drug composition according to claim 1.

4. The method of claim 3, wherein the central nervous system disorder is characterized by excessive neuronal activity or inflammation.

5. The method of claim 3, wherein the central nervous system disorder is selected from the group consisting of ischemia, Alzheimer's disease, multiple sclerosis and anxiety.

6. The method of claim 3, wherein the nanoparticle carrier has a mean particle size of between about 100 nm and about 250 nm.

7. A method of generating a nanoparticle suspension comprising: nanoprecipitation of a polymer, further comprising dissolving or diluting poly(lactic-co-glycolic acid) conjugated with polyethylene glycol (PLGA-PEG) in acetone to form a polymer solution; dissolving a predetermined quantity of afobazole in ethanol to form a drug solution; adding the drug solution to the polymer solution to form an organic phase solution; adding the organic phase solution to deionized water to form a mixture; stirring the mixture; evaporating the acetone from the mixture wherein upon evaporation of the acetone a suspension of nanoparticles is generated; and coating the suspension of nanoparticles with a hydrophilic antioxidant.

8. The method of claim 7, wherein the hydrophilic antioxidant is glutathione.

9. The method of claim 7, wherein the acetone is evaporated overnight at room temperature.

* * * * *